US00PP35632P2

(12) United States Plant Patent
Bacon et al.

(10) Patent No.: US PP35,632 P2
(45) Date of Patent: Feb. 6, 2024

(54) CHERRY TREE NAMED 'SUCHERRY2'

(50) Latin Name: ***Prunus avium* L.**
Varietal Denomination: Sucherry2

(71) Applicant: Sun World International, LLC, Bakersfield, CA (US)

(72) Inventors: Terry A. Bacon, Maplewood, NJ (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 18/102,950

(22) Filed: Jan. 30, 2023

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
CPC ... A01H 5/08; A01H 5/00; A01H 6/74; A01H 6/7445
See application file for complete search history.

(56) References Cited

U.S. PATENT DOCUMENTS

PP6,407 P * 11/1988 Bradford ..... Plt./181
PP12,942 P2 * 9/2002 Zaiger ..... A01H 5/08 Plt./181

OTHER PUBLICATIONS

Foundation Plant Services UC Davis, retrieved on May 16, 2023 at https://fps.ucdavis.edu//treedetails.cfm?v=4623, one page. (Year: 2023).*

* cited by examiner

*Primary Examiner* — June Hwu
(74) *Attorney, Agent, or Firm* — Knobbe, Martens, Olson & Bear, LLP

(57) ABSTRACT

The new variety of cherry tree named 'Sucherry2', substantially is characterized by very early ripening, very large-size fruit with dark red flesh and dark red skin.

1 Drawing Sheet

Latin name of the genus and species claimed: *Prunus avium* L.

Variety denomination: 'Sucherry2'.

BACKGROUND AND SUMMARY OF THE INVENTION

This invention relates to the discovery and asexual propagation of a new and distinct variety of cherry tree, *Prunus avium* L., named 'Sucherry2'. The new variety was first selected in April 2017 by Terry A. Bacon and Terrence J. Frett as breeder number 'CH2023'. The new variety was first evaluated by Terry A. Bacon and Terrence J. Frett near Wasco, California in Kern County. The variety 'Sucherry2' was originated by hybridization.

The new variety 'Sucherry2' is characterized by very early ripening, very large-sized fruit with dark red flesh and dark red skin.

The seed parent is 'Cherry-2' (unpatented) and the pollen parent is 'LCCherry2' (unpatented). The parent varieties were first crossed in February 2014, with the date of first sowing being February 2015 and the date of first flowering being February 2017. The new cherry variety 'Sucherry2' was first asexually propagated by Terry A. Bacon and Terrence J. Frett near Wasco, Kern County, California in February 2018 by dormant grafting.

The new variety 'Sucherry2' is similar to its seed parent 'Cherry-2' (unpatented) in that they both have similar shaped fruit. However, the bloom of the new variety 'Sucherry2' starts 20 days earlier than for 'Cherry-2' and harvest starts about 11 days earlier than for 'Cherry-2'.

The new variety 'Sucherry2' is similar to its pollen parent 'LCCherry2' (unpatented) in that they both have similar shaped fruit. However, the bloom of the new variety 'Sucherry2' starts 13 days earlier than for 'LCCherry2' and harvest starts about 3 days earlier than for 'LCCherry2'.

The harvest of the fruit of the new variety 'Sucherry2' starts about 13 days earlier than 'Tulare' (U.S. Plant Pat. No. 6,407) and the fruit shape of the new variety is reniform compared to cordate for 'Tulare'. The new variety 'Sucherry2' also differs from 'Tulare' in that the chilling requirement is 450 chill units compared to 400 chill units for 'Tulare'.

The new variety 'Sucherry2' has a similar fruit shape as 'Bing' (unpatented), but the harvest of the new variety 'Sucherry2' starts about 19 days earlier than that of 'Bing'. The frequency of double pistils in the new variety 'Sucherry2' is rare compared to frequent for 'Bing'.

The new variety 'Sucherry2' has a similar fruit shape as 'Brooks' (unpatented), but the harvest of the new variety 'Sucherry2' starts about 14 days earlier than that of 'Brooks' and the bloom for Sucherry2' starts about 25 days earlier than that of 'Brooks'.

The new variety 'Sucherry2' has a similar fruit shape and frequency of double pistils as 'Sucherryone' (U.S. Plant Pat. No. 30,730), but the ripening of the new variety 'Sucherry2' starts about 4 days earlier than that of 'Sucherryone'. The new variety 'Sucherry2' also differs from 'Sucherryone' in that the chilling requirement is 450 chill units compared to 750 chill units for 'Sucherryone'.

The rare frequency of double pistils is the same for the new variety 'Sucherry2' as for 'Minnie Royal' (U.S. Plant Pat. No. 12,942), but the fruit shape of the new variety is reniform compared to cordate for 'Minnie Royal'. The new variety 'Sucherry2' also differs from 'Minnie Royal' in that the chilling requirement for 'Sucherry2' is 450 chill units compared to 400-500 chill units for 'Minnie Royal' and the harvest of the new variety 'Sucherry2' starts about 3 days earlier than that of 'Minnie Royal'.

The new variety 'Sucherry2' has been shown to maintain its distinguishing characteristics through successive asexual propagations by, for example, cuttings and grafting.

BRIEF DESCRIPTION OF THE DRAWING

The accompanying color photographic illustration taken of a 4-year-old plant shows typical specimens of the foliage and fruit of the present new cherry variety 'Sucherry2'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to 5 year old 'Sucherry2' trees grown in the vicinity of Wasco, Kern County, California during 2017, and is believed to apply to plants of the variety grown under similar conditions of soil and climate elsewhere.

TREE

General: (Measurements taken on 5-year-old trees unless otherwise noted.).

- *Size*.—Medium. Reaches a height of approximately 3 meters with normal pruning.
- *Vigor*.—Strong. Top shoot growth of about 1.5 meters during the first growing season.
- *Growth*.—Semi-upright.
- *Productivity*.—Productive. Produces ample fruit set annually.
- *Fertility*.—Self-incompatible; pollinator required.
- *Hardiness*.—Hardy in all fruit growing areas of California. Winter chilling requirement is approximately 450 hours at or below 7.2° C.
- *Disease resistance/susceptibility*.—No specific testing for relative plant disease resistance/susceptibility has been undertaken. Under close observation in Kern County, California, no particular plant/fruit disease resistance/susceptibility has been observed.
- *Habit*.—Upright.
- *Vigor*.—Vigorous.
- *Spread*.—Intermediate spreading branch pattern.
- *Branching strength*.—Strong, but with manageable branches that are at an intermediate angle.

Trunk: (Measurements at approximately 30 cm above the soil line.).

- *Diameter*.—Approximately 27 cm.
- *Texture*.—Medium shaggy; increases with age of tree.
- *Trunk color*.—About Light Black 202C with highlights of Dark Greyed-Orange 176B, becoming darker with age.

Branches: (Measurements at approximately 90 cm above the soil line.).

- *Diameter*.—Approximately 14 cm.
- *Texture*.—Medium shaggy; increasing with tree age.
- *Color*.—About Light Black 202C with highlights of Medium Greyed-Orange 176C, becoming darker with age.
- *Lenticels density*.—Approximately 0-2 per $cm^2$.
- *Lenticels color*.—About Medium Greyed-Green 198B.
- *Lenticels length*.—Approximately 10 mm.
- *Lenticels width*.—Approximately 3 mm.

Shoots: (Data taken in May at the midpoint of current-season growth.).

Young shoots:

- *Anthocyanin coloration of apex (during raping growth)*.—Weak.
- *Pubescence of apex during rapid growth*.—Medium.

Current season shoots:

- *Thickness at midlength*.—Medium; approximately 7 mm.
- *Length of internodes*.—Normal; mostly 2 cm.
- *Color topside*.—About Light Green 138C.
- *Color underside*.—About Light Green 138C.
- *Lenticels density*.—Few; about 1 per $cm^2$.
- *Lenticels color*.—About Medium Greyed-Green 198B.
- *Lenticel dimensions*.—Width: Approximately 1 mm. Length: Approximately 2 mm.
- *Presence of anthocyanin coloration*.—Absent or very sparse.

One year old shoots:

- *Number of flower buds per spur*.—About 10, varies from 4 to 12.

FOLIAGE

Leaves: (data taken in September at the midpoint of current-season growth).

- *Average length*.—Long; approximately 14 cm without petiole.
- *Average width*.—Broad; approximately 7 cm.
- *Length:width ratio*.—Medium; about 2:1.
- *Shape*.—Elliptic.
- *Color of upper side and intensity*.—Medium intensity; about Dark Green 136B.
- *Color of lower side*.—About Light Green 138C.
- *Angle at base*.—Rounded.
- *Angle at apex*.—Acuminate.
- *Vein color*.—About Light Green 139D.
- *Presence of red coloration of mid-vein on the lower side*.—Absent.
- *Surface texture*.—Smooth on both top and bottom surfaces.
- *Shape in the cross section*.—Slightly up-folded.
- *Leaf blade tip*.—In the plane of the leaf.
- *Undulation of margin*.—Slight.
- *Margin*.—Shallow serrate.
- *Ratio length of leaf blade:length of petiole*.—Medium: 3.5:1.

Petiole:
*Average length*.—Medium; approximately 32 mm.
*Average diameter*.—Approximately 2 mm.
*Color*.—About Medium Green 139C.
Stipules:
*Number/leaf bud*.—Usually 2.
*Typical length*.—Approximately 11 mm.
*Color*.—About Dark Greyed-Orange 166A when dried.
*Persistence*.—Falls off.
Glands (nectaries):
*Form*.—Reniform.
*Average number and arrangement*.—Usually 2, alternating. Predominately on petiole.
*Dimension*.—Approximately 2 mm long by 1.4 mm wide.
*Color*.—About Dark Greyed-Red 178B in September.
Vegetative buds: (Data taken in September at midpoint of current-season growth).
*Bud dimensions*.—Approximately 10 mm long by 4 mm wide.
*Bud shape*.—Conical.
*Color*.—About Dark Greyed-Orange 177A.

FLOWERS

General:
*Type of bloom*.—Showy.
*Diameter of fully opened flower*.—Medium, approximately 27 mm.
*Flower aroma*.—Medium-strong.
*Time of beginning of flowering*.—Very early.
*Flower blooming period*.—First Bloom: Approximately February 19. Full Bloom: Approximately March 1.
*Location of first bloom*.—Tips of one-year-old shoots.
*Location of full bloom*.—Central part of the tree canopy.
*Duration of bloom*.—Approximately 12 days.
Flower buds: (Data taken in September at midpoint of current-season growth).
*Bud dimensions*.—Approximately 8 mm long by 3 mm wide.
*Bud shape*.—Conical.
*Color*.—About Dark Greyed-Orange 177B.
*Number of flowers per flower bud*.—Average 4; varies from 2 to 6.
*Number of buds per spur*.—Average 7; varies from 5 to 10.
Pedicels:
*Length*.—Approximately 12 mm.
*Color*.—About Medium Green 138B.
Sepals:
*Number*.—5.
*Shape*.—Triangular.
*Position*.—Adpressed to petals, alternate with petals.
*Length*.—Approximately 7 mm.
*Width*.—Approximately 5 mm.
*Surface texture*.—Glabrous on outer and inner surfaces.
*Color of lower surface*.—About Dark Greyed-Purple 184A.
*Color of upper surface*.—About muted Dark Greyed-Purple 184A.
Petals:
*Number*.—5.
*Arrangement*.—Usually free.
*Color of lower and upper surfaces*.—About White 155A.
*Surface texture*.—Smooth on upper and lower surface.
*Dimensions*.—Approximately 16 mm long by 14 mm wide.
*Shape*.—Circular.
*Apex shape*.—Rounded.
*Base shape*.—Narrows at point of attachment.
*Undulation of margins*.—Medium.
*Frequency of flowers with double petals*.—Rare.
Stigma:
*Position compared to anthers*.—Slightly higher.
Stamens:
*Number*.—About 38; varies from 34 to 40.
*Filament length*.—Average 12 mm.
*Filament color*.—About White 155A.
*Pollen*.—Present.
*Flower pollen color*.—About Light Yellow 3D.
Pistil:
*Length*.—Approximately 16 mm.
*Surface*.—Glabrous.
*Frequency of supplementary pistils*.—Rare.

FRUIT

General: (Description taken at firm-mature near Wasco, Kern County, California).
*Date of first pick*.—Approximately April 24.
*Date of last pick*.—Approximately May 4.
*Time of beginning of fruit ripening*.—Very early.
Stem:
*Length*.—Medium, approximately 30 mm.
*Thickness*.—Medium, approximately 2 mm.
*Color*.—About Light Green 139D.
*Abscission layer between stalk and fruit*.—Absent.
Fruit size:
*Size*.—Very large.
*Weight*.—About 10 g.
*Height*.—About 23 mm.
*Diameter perpendicular to suture*.—Approximately 26 mm.
*Diameter ventral side, facing suture*.—Approximately 28 mm.
Fruit shape:
*Shape viewed from apex*.—Oblate.
*Shape ventral side, facing suture*.—Reniform.
*Symmetry viewed from pistil end*.—Symmetric or slightly asymmetric.
*Shape of pistil end*.—Slightly depressed.
*Depth of stem cavity*.—Medium, about 1.8 mm.
*Width of stem cavity*.—Medium, about 4 mm.
*Promenence of suture*.—Absent or very weakly conspicuous.
Fruit skin:
*Thickness*.—Intermediate, typical of most varieties.
*Adherence to flesh*.—Strong.
*Taste*.—Neutral.
*Surface texture*.—Smooth.
*Bloom*.—Wanting.
*Tendency to crack*.—None during dry weather. Slight tendency to crack in wet weather but varies with stage of maturity.
*Size of lenticels on skin*.—Absent or very small.
*Number of lenticels on skin*.—Medium, approximately 12 per $cm^2$.

*Color*.—About Dark Red 59A, becoming Dark Purple 79A with ripening.

Flesh:

*Ripens*.—Evenly.

*Color*.—At full maturity about Dark Red 53B to Dark Red 53A.

*Color of juice*.—About Light Red 53D at full maturity.

*Flavor*.—Sweet-mild.

*Firmness*.—Firm; comparable to most commercial varieties.

*Juiciness*.—Medium; able to squeeze free juice easily.

*Sweetness*.—Medium; about 19% brix at harvest.

*Acidity*.—Medium for cherries; about 0.79% titratable acidity.

*Texture*.—Firm.

*Fibers*.—Few, small and tender.

Stone:

*Stone size*.—Medium. Length: Approximately 10 mm. Diameter Facing Suture: Approximately 7 mm. Diameter Perpendicular to Suture Plane: Approximately 10 mm.

*Ratio weight of fruit:weight of stone*.—Medium, about 55:1.

*Color*.—About Medium Greyed-Yellow 161C when dried.

*Shape in lateral view perpendicular to suture*.—Circular.

*Shape in ventral view facing suture*.—Broad elliptic.

*Shape in basal view*.—Broad elliptic.

*Base shape*.—Flat.

*Apex shape*.—Rounded.

*Ridges*.—A small narrow ridge on each side of suture, extending from base to apex.

*Symmetry in lateral view*.—Symmetric or slightly asymmetric.

*Surface*.—Nearly smooth except for small ridges near the suture.

*Width of stalk end*.—Narrow, approximately 1 mm.

*Tendency to split*.—None.

*Adherence to flesh*.—Semi-freestone.

Market:

*Use*.—Dessert.

*Market*.—Local and long distance.

*Storage quality*.—Good, held well for 4 weeks in cold storage at 33° F. and maintained good appearance and eating quality.

*Shipping quality*.—Good, showed minimal bruising or scarring during harvest, packing and shipping trials.

What is claimed is:

1. A new and distinct variety of cherry tree named 'Sucherry2', substantially as herein described and illustrated.

* * * * *

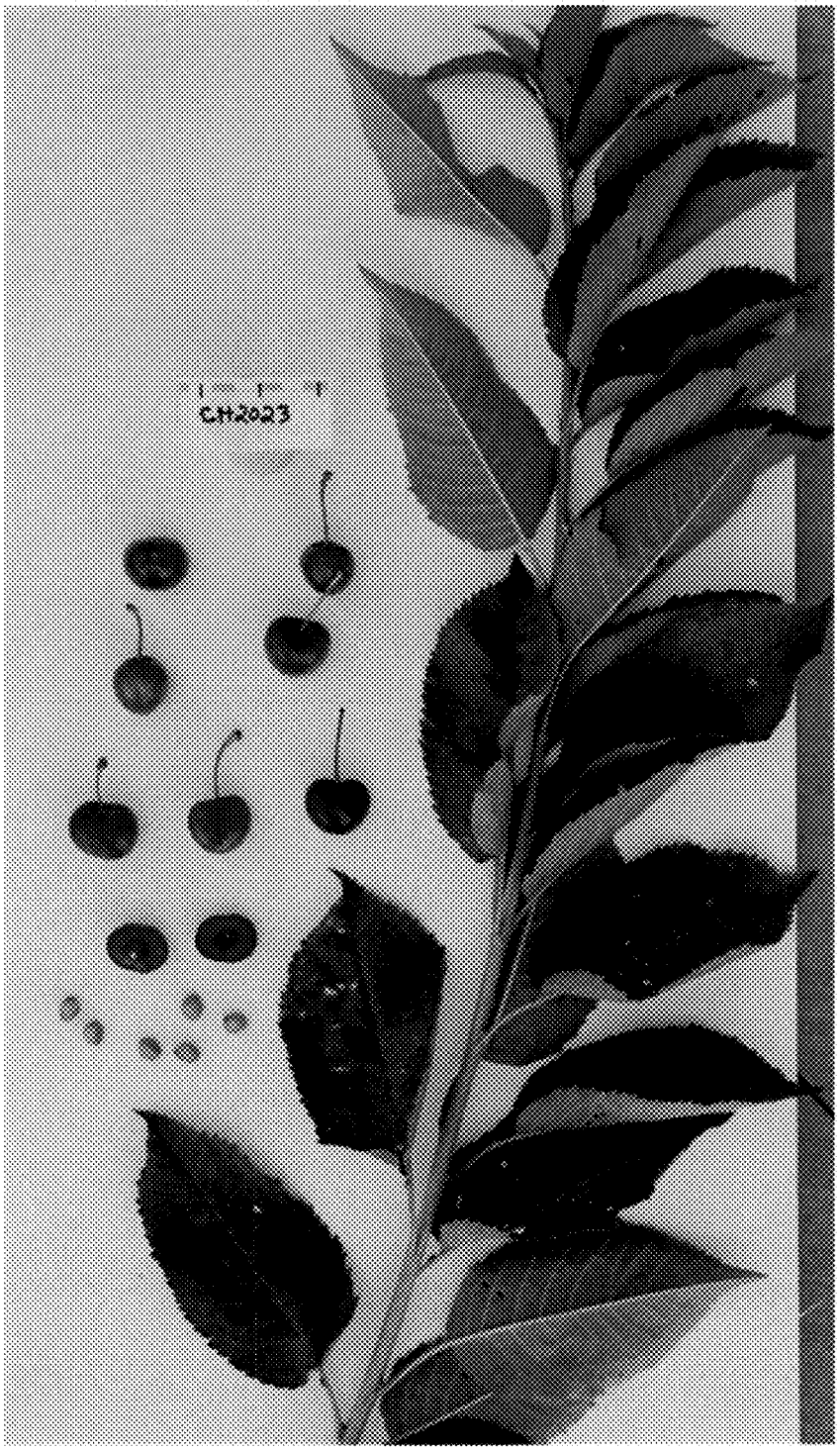
CH2023